United States Patent
Dick et al.

(10) Patent No.: US 11,660,231 B2
(45) Date of Patent: *May 30, 2023

(54) METHOD FOR MINIMALLY INVASIVE, CELL-SELECTIVE LASER THERAPY ON THE EYE

(71) Applicant: Carl Zeiss Meditec AG, Jena (DE)

(72) Inventors: Manfred Dick, Gefell (DE); Gerald Kunath-Fandrei, Jena (DE); René Denner, Reisdorf (DE); Thomas Wurlitzer, Leipzig (DE)

(73) Assignee: Carl Zeiss Meditec AG, Jena (DE)

( * ) Notice: Subject to any disclaimer, the term of this patent is extended or adjusted under 35 U.S.C. 154(b) by 135 days.

This patent is subject to a terminal disclaimer.

(21) Appl. No.: 17/202,530

(22) Filed: Mar. 16, 2021

(65) Prior Publication Data

US 2021/0196519 A1 Jul. 1, 2021

Related U.S. Application Data

(63) Continuation of application No. 16/090,495, filed as application No. PCT/EP2017/058381 on Apr. 7, 2017, now Pat. No. 10,973,687.

(30) Foreign Application Priority Data

Apr. 8, 2016 (DE) ..................... 10 2016 205 914.9

(51) Int. Cl.
*A61F 9/008* (2006.01)
*A61F 9/007* (2006.01)
*A61F 9/009* (2006.01)

(52) U.S. Cl.
CPC .......... *A61F 9/00821* (2013.01); *A61F 9/008* (2013.01); *A61F 9/009* (2013.01);
(Continued)

(58) Field of Classification Search
CPC .. A61F 9/00821; A61F 9/00781; A61F 9/008; A61F 9/009; A61F 2009/00863; A61F 2009/00868; A61F 2009/00891
See application file for complete search history.

(56) References Cited

U.S. PATENT DOCUMENTS 5,549,596 A 8/1996 Latina
8,568,393 B2 10/2013 Palanker
(Continued)

OTHER PUBLICATIONS

Kurtz et al., "Photodisruption in the Human Cornea as a Function of Laser Pulse Width", Journal of Refractive Surgery, vol. 13, Nov./Dec. 1997, pp. 653-658.
(Continued)

*Primary Examiner* — Paula J Stice
(74) *Attorney, Agent, or Firm* — DeWitt LLP (57) ABSTRACT

A method for a minimally invasive, cell-selective laser therapy on the eye. The method, based on a short-pulse laser system, allows for different selective types of therapy on the eye. The method is based on a frequency-doubled, continuously working solid-state laser including a pump source and a control unit. The control unit regulates the pump source such that the solid-state laser emits individual pulses with pulse lengths ranging from 50 ns to continuous, wherein pulse lengths ranging from 50 ns to 50 μs are provided for selective therapies and pulse lengths ranging from 50 μs to continuous are provided for coagulative or stimulating therapies, in particular in the range from 1 ms to 500 ms. The proposed method enables a selective treatment of melanin-containing cells in the different areas of the eye via the targeted control of the pump source.

33 Claims, 5 Drawing Sheets

(52) U.S. Cl.
CPC .................... *A61F 9/00781* (2013.01); *A61F 2009/00863* (2013.01); *A61F 2009/00868* (2013.01); *A61F 2009/00891* (2013.01); *A61F 2009/00897* (2013.01)

(56) References Cited

U.S. PATENT DOCUMENTS

| | | |
|---|---|---|
| 2006/0161145 A1 | 7/2006 | Lin |
| 2006/0187978 A1 | 8/2006 | Telfair |
| 2009/0287138 A1 | 11/2009 | Latina |
| 2015/0111275 A1* | 4/2015 | Palanker ................ C12N 15/86 606/4 |

OTHER PUBLICATIONS

Application and File History for U.S. Appl. No. 16/090,495, filed Oct. 1, 2018. Inventors: Manfred Dick et al.

* cited by examiner

METHOD FOR MINIMALLY INVASIVE, CELL-SELECTIVE LASER THERAPY ON THE EYE

CROSS-REFERENCE TO RELATED APPLICATIONS

This application is a continuation of application Ser. No. 16/090,495 filed Oct. 1, 2018, which in turn is a National Phase entry of PCT Application No. PCT/EP2017/058381, filed Apr. 7, 2017, which application claims benefit of priority to German Application 10 2016 205 914.9, filed Apr. 8, 2016, each of which is hereby fully incorporated herein by reference.

TECHNICAL FIELD

The present invention relates to a method for a minimally invasive, cell-selective laser therapy (short: CSLT) on the eye. The method, based on a short-pulse laser system, permits different selective types of therapy on the eye.

BACKGROUND

Various systems of selectively working lasers for a therapeutic laser therapy on the eye are not only used in the research for years but are also used in the clinical environment. In order to use the absorption properties in the eye in a suitable manner for this method, a wavelength particularly in the green, yellow, red, and infrared spectral range is known. The selective absorption is known in particular for melanin-containing cells in the eye, wherein particularly lasers in the green spectral range are used in this case, since a high absorption coefficient of melanin is present for wavelengths of e.g. 532 nm when compared to longer wavelengths.

As the most well-known methods of the selective laser therapy on the eye, the selective laser trabeculoplasty (short: SLT), the selective retina therapy (short: SRT) and the retina regeneration therapy (short: 2RT) can be mentioned.

The SLT is a simple and highly effective laser therapy in the field of the trabecular meshwork, which reduces the intraocular pressure in glaucoma. The trabecular meshwork is a spongy mesh in the area of the anterior chamber angle which is visible by gonioscopy. The continuously produced aqueous fluid drains through this mesh, which ensures the health of the cornea and of the lens. If the trabecular meshwork in the eye hardens, an unobstructed draining is no longer possible, the aqueous fluid accumulates in the eye and leads to an increase of the intraocular pressure—the glaucoma. In addition to the selective absorption of particularly the wavelength 532 nm in the pigment melanin, the SLT laser therapy uses very short light pulses with low energy and thus only targets the specific melanin or pigment cells in the trabecular meshwork of the eye. Depending on the energy density, these cells are either stimulated or destroyed and thereafter renewed or removed by means of a regenerative, self-healing process of the body. In this natural manner, the draining of the aqueous fluid is improved, and the intraocular pressure is reduced.

The main features of an SLT-method, which is also referred to as selective laser trabeculoplasty, are described e.g. in the writings of the U.S. Pat. No. 5,549,596 A. In this method for the treatment of glaucoma, intraocular melanoma and macular edema, the irradiation of the corresponding area is performed with a laser radiation ranging between approx. 0.01 and approx. 5 Joules/cm$^2$.

The solution described in the U.S. Pat. No. 8,568,393 B2 also relates to an SLT method, wherein the treatment has been optimized by the use of scanners.

A laser system that is used for the SLT method is described in [1], a product brochure of the Ellex company (http://www.ellex.com/de/). The SLT treatment is carried out at a wavelength of 532 nm, with a pulse length of 3 ns and a pulse energy of approx. 1 mJ on a spot diameter of 400 µm in the trabecular meshwork of the eye, wherein the treatment can be carried out on a circumference of 1800 or even 360°.

On the other hand, SRT refers to laser treatments of macular diseases. A number of macular diseases can be successfully treated by application of a conventional laser treatment, yet it is accepted that the intact retina is hereby destroyed. For many macular diseases, which are merely associated with a limited function of the retinal pigment epithelium (short: RPE), a selective laser treatment of these cells may be the ideal treatment. With the SRT, the RPE is selectively treated in the irradiated area by means of microsecond laser pulses. Micro vaporization on the melanin granules in the cell causes the photo disruption of the irradiated cells, while the adjacent neurosensory retina with the photoreceptors and the choroid under the RPE is not damaged. The therapy ideally leads to a regeneration of the RPE.

In contrast to the established laser photocoagulation, in which the irradiated and surrounding areas of the retina are destroyed, scotomas are completely prevented in the SRT. However, the laser effects are herein not visible to the attending physician during the therapy and can only be recognized by means of a subsequent fluorescence angiography on the irradiated areas.

The 2RT laser therapy is used to regenerate the retina and macula. This new laser therapy is the first available treatment for age-related macular degeneration in its early stages, which is also referred to as dry macular degeneration. It is performed with a special short pulse laser and can stimulate the regeneration of the retina, due to which it is also called retinal regeneration therapy (2RT). Since it is also much gentler than the laser coagulation, the treatment may also be applied in the area of the macula. The non-invasive method is furthermore a possible and gentler alternative to the laser coagulation for the diabetes-induced macular edema. A very good effect is also achieved in the treatment of Chorioretinopathy Centralis Serosa (also referred to as Central Serous Chorioretinopathy). The laser therapy aims to stimulate the natural regeneration process of the retinal pigment epithelium (RPE) on the macula, in that only the inside of individual RPE cells is destroyed. Since this RPE cell then no longer performs its tasks, the natural regeneration is stimulated and a new cell is formed.

SUMMARY

Since the selectively working laser systems that are known thus far in line with the prior art are only based on a fixed, non-modifiable pulse length, these cannot be used universally. A system with a particularly intraoperatively selectable pulse length for a selectable selectivity of the damage of the entire cell or of only cellular components, is not known thus far. Furthermore, it has proven to be a disadvantage in the well-known selectively working laser systems, that no patterns are used, which allow for an intracellular or cellular destruction in a structured manner.

Since only spot sizes are used up to now, without taking into account the thermal damage zones, the attending physician can basically not give any clear therapeutic statement regarding the effective therapeutic effect of the laser treatment.

Example embodiments of present invention are based on development of a method for a minimally invasive, cell-selective laser therapy on the eye, which eliminates the disadvantages of the prior art and which enables the selective treatment of melanin-containing cells in the different areas of the eye, in particular of the trabecular meshwork, of the retinal pigment epithelium and of the iris.

In line with the invention, this objective is achieved by means of the proposed method for a minimally invasive, cell-selective laser therapy on the eye, based on a frequency-doubled, continuously working solid-state laser with a pump source and a control unit, in that the control unit regulates the pump source in such a way that the solid-state laser continuously emits individual pulses with pulse lengths ranging from 50 ns to continuous, wherein pulse lengths ranging from 50 ns to 50 µs are provided for selective therapies and pulse lengths ranging from 50 µs to continuous, in particular in the range of 1 ms to 500 ms are provided for coagulative or stimulating therapies.

Example embodiments of a method for a minimally invasive, cell-selective laser therapy on the eye does not only enable a laser trabeculoplasty as glaucoma therapy by application of a targeted controlling of the pump source, but it enables a selective treatment of melanin-containing cells in the different areas of the eye, based on a scanning ns-laser system.

The above summary is not intended to describe each illustrated embodiment or every implementation of the subject matter hereof. The figures and the detailed description that follow more particularly exemplify various embodiments.

BRIEF DESCRIPTION OF THE DRAWINGS

In the following, the invention is explained in more detail by means of embodiments. It is hereby shown.

While various embodiments are amenable to various modifications and alternative forms, specifics thereof have been shown by way of example in the drawings and will be described in detail. It should be understood, however, that the intention is not to limit the claimed inventions to the particular embodiments described. On the contrary, the intention is to cover all modifications, equivalents, and alternatives falling within the spirit and scope of the subject matter as defined by the claims.

DETAILED DESCRIPTION OF THE DRAWINGS

The proposed example method for a minimally invasive, cell-selective laser therapy on the eye is based on a frequency-doubled, continuously working solid-state laser comprising a pump source and a control unit. According to the invention, the control unit regulates the pump source in such a way that the solid-state laser emits individual pulses with pulse lengths ranging from 50 ns to continuous, wherein pulse lengths ranging from 50 ns to 50 µs are provided for selective therapies and pulse lengths ranging from 50 µs to continuous are provided for coagulative or stimulating therapies, in particular in the range from 1 ms to 500 ms.

It is particularly preferred, for example, that the control unit regulates the pump source in such a way that the solid-state laser emits individual pulses with pulse lengths ranging from 50 ns to 50 µs, wherein the energy density of the individual pulses varies in dependence of the pulse length. Particularly individual pulses with pulse lengths in the range of 50 ns-500 ns and in the range of 1 µs-50 µs are emitted in a variable manner.

While the individual pulses with pulse lengths in the rage of 50 ns to 500 ns are used for the selective destruction of melanozomes within a cell or within a melanocyte, the individual pulses with pulse lengths in the range of 1 µs to 50 µs are used for the selective destruction of whole melanocyte cells. In addition to the use of the laser system on a level above the threshold for the selective destruction of these tissue components, a subliminal selective excitation of particularly the melanin-containing absorbers is furthermore intended in order to stimulate these for healing processes. The energy density is hereby chosen in such a way that no intracellular or cellular blistering occurs.

This results from the different energy densities of individual pulses of the respective pulse length ranges. The energy density of an individual pulse at pulse lengths ranging from 50 ns to 500 ns lies at >50 mJ/cm$^2$ and at pulse lengths ranging from 1 µs to 50 µs, it lies at >500 mJ/cm$^2$.

Spot sizes ranging from 50 µm to 100 µm are preferably used for the laser therapy, wherein the spots can be bundled in the form of patterns. The spot sizes used for the laser therapy can be generated by means of one or also several individual pulses.

The repetition rate of the laser pulses is provided for example from 1 Hz to 10 kHz, in particular for example from 100 Hz to 2 kHz.

If several individual pulses are applied for one spot, then a constant pulse length and/or pulse energy or a variable pulse length and/or pulse energy is provided as a choice.

In accordance with the invention, it is also possible to vary the spot distance within the pattern in addition to the shape of the pattern. For example, sequential laser spot positioning within a pattern is used, which is based on a continuous movement of the scanner. For example, a spiral is provided for a circular pattern. The track speed of the scanned laser beam is synchronized with the repetition rate of the laser in such a way, that the laser spots are applied in close contact (touching) or with a defined distance at the tissue within a pattern. In a dense packing for a complete covering of the surface of the tissue, square laser spots are provided, which are set tightly/adjacently next to each other. In this way a therapy that covers the entire surface is to be made possible with the laser pattern, which is otherwise only possible by application of a laser with a very high pulse energy and a homogeneous beam profile.

It is furthermore possible, that the control unit regulates the pumping current of the pump source in such a way that the pulse lengths and thus the energy density of the individual pulses of an entire pattern or also of the individual pulses can be varied within a pattern. The pulse peak power and thus the pulse energy can thus be adjusted online from spot to spot within a pattern after having preselected the pulse length.

According to an example embodiment, the pulse lengths and thus the energy density of the individual pulses of an entire pattern or also of the individual pulses within a pattern are alternating. The purpose of this alternating sequence is that pulse lengths ranging from 50-500 ns and from 1-50 µs are provided to selectively destroy alternately melanocytes in the cell or the entire cell.

It is furthermore essential for the invention that one or more parameter sets are predetermined by the control unit in an operating menu for various selective forms of therapy in the eye.

It is intended to predetermine parameter sets in the operating menu of the solid-state laser for the various selective forms of therapy in the eye, such as e.g. for the selective laser trabeculoplasty, the selective retinal therapy, the laser-based capsulorhexis (in particular anterior, but also posterior for the treatment of the aftercataract) and the retinal regeneration therapy.

The following parameters are taken into account in the parameter sets of the operating menu of the control unit: spot size, spot distance, shape of the pattern, pulse length, energy density and number of pulses as well as the repetition rate.

According to an example embodiment of the method, the solid-state laser for selective laser trabeculoplasty, for selective retinal therapy and for retinal regeneration therapy emits individual pulses with pulse lengths in the range of 50 ns-500 ns, for example 200 ns and in the range of 1 µs-50 µs, in particular 5 µs.

By way of comparison, it should be mentioned at this point that laser pulses with a pulse length of 1 ns-3 ns are used to carry out the SLT and the 2RT therapy in accordance with the known prior art. For the SRT therapy, pulse lengths of 1.7 µs and energy densities of 150-250 µJ are finding application, wherein up to 30 pulses are being emitted per spot.

According to the invention for the selective laser trabeculoplasty, spot sizes of 50 µm to 100 µm are provided for an individual pulse, which are set in a dense packing, in particular as a square spot adjacent to each other. Hereby maximum patterns of 400×400 µm² are generated in the trabecular meshwork.

In a particularly practical example version for the selective laser trabeculoplasty, individual pulses are applied with the following parameters:
Pulse lengths in the range of 50 ns-500 ns, in particular 200 ns,
Pulse energies of 2-50 µJ, in particular 25 µJ,
Square spot with an edge length of 50 µm,
Spot patterns with square spots that are directly set adjacent to each other with an outer, approximately octagonal shape with a diameter of 400 µm.

The treatment of the trabecular meshwork is hereby carried out by application of the directly adjacent arrangement of these hexagonal patterns along the circumference of the trabecular meshwork in the eye. Wherein approx. 180° or also the entire 3600 are treated in one session.

By using a square fiber, the individual laser spots can be set directly adjacent to each other and generate a very homogeneous, octagonal pattern, by application of which an optimal laser therapy is made possible. Compared to circular fiber diameters, an improved mode mixture is achieved with square fibers, which further facilitates the generation of homogeneous patterns.

Figure 1:
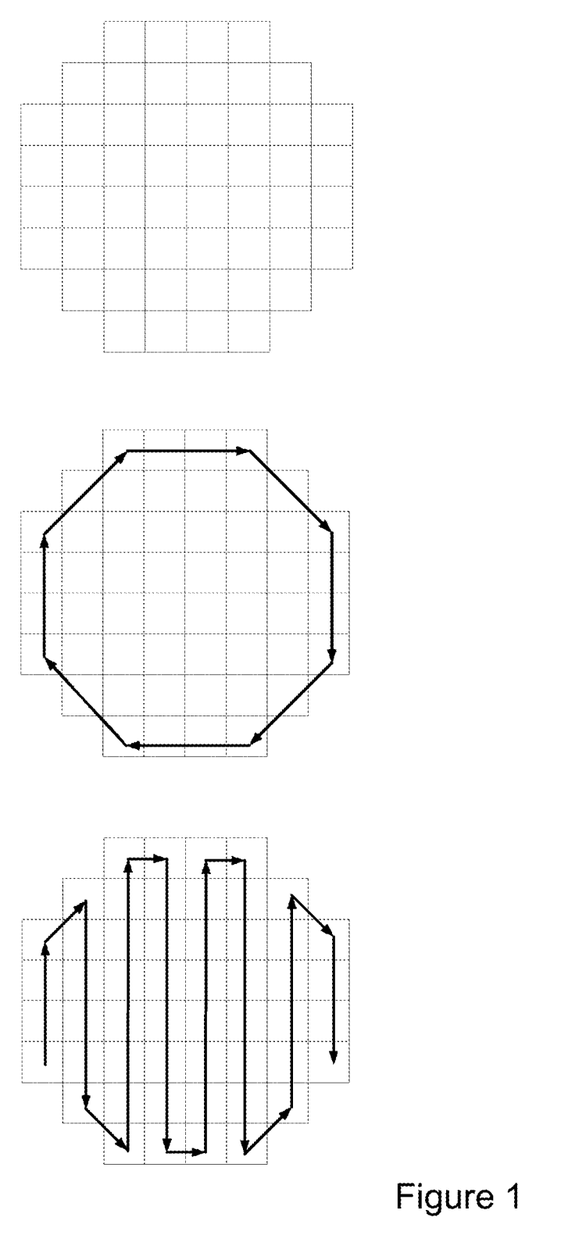
FIG. 1 depicts an octagonal pattern that is made up of 52 square laser spots.

In this connection, FIG. 1 depicts such an octagonal pattern. As shown in the upper depiction, the pattern is made up of 52 square laser spots.

To display the position of the pattern that is to be applied to the operator, the complete outer contour of the entire pattern is followed in line with the invention. It is also possible that only the outer corners of the pattern and/or the center point is depicted. This can be derived from the center depiction of FIG. 1.

From the lower depiction of FIG. 1 it can be seen that the generation of this octagonal pattern is carried out according to the invention by following a meander-like course, wherein only the coordinates of the reversing points are targeted and all the individual points in between are only traversed. An application of all individual laser spots is only carried out after an exact position feedback of the measuring system.

The speed of the application of the entire pattern can be achieved in that the track speed of the scanner is only reduced at the reversing points. At the reversing points, the laser spot is only applied after the position feedback by means of the measuring system.

When the track speed of the scanner is known, a pinpointed stringing of the individual spots is furthermore only possible by means of a precise timing control. In this way it is e.g. possible to apply the 52 spots of the octagonal pattern within a time of <280 ms.

According to a further advantageous example embodiment of the method, the solid-state laser emits a laser wavelengths in the green or yellow spectrum for the selective destruction of lipofuscin in the retina, in particular 532 nm, 561 nm, 577 nm or 586 nm.

Lipofuscin is a degradation product of the metabolism that is remaining on the ocular fundus in the form of a granulate with individual sizes of 1-2 µm diameter and it can accumulate in drusen. The deviating wavelength hereby results from the absorption wavelength of the lipofuscin which is different from melanin.

By the selective destruction or crushing of the granules of the lipofuscin, the metabolism of the retina is reactivated so that it can dispose of these disturbing components and to prevent eye diseases such as e.g. the age-related macular degeneration (AMD).

The destruction of the lipofuscin can hereby be carried out e.g. directly within the drusen or the decomposing of the drusen is stimulated by application of the selective treatment of the RPE also outside the drusen areas.

For the treatment, the laser system can be operated both in the single-shot mode as well as in the pattern mode.

The individual spots are hereby applied as circular spots with a diameter of >/=50 µm or as square spots with an edge length of >/=50 µm. Optionally, these can be positioned by the physician at the fundus of the eye for the therapy.

In the pattern mode, circular or square laser spots are provided, which can be composed into overall patterns to cover the entire surface or also with a distance of at least one spot size.

Figure 2:
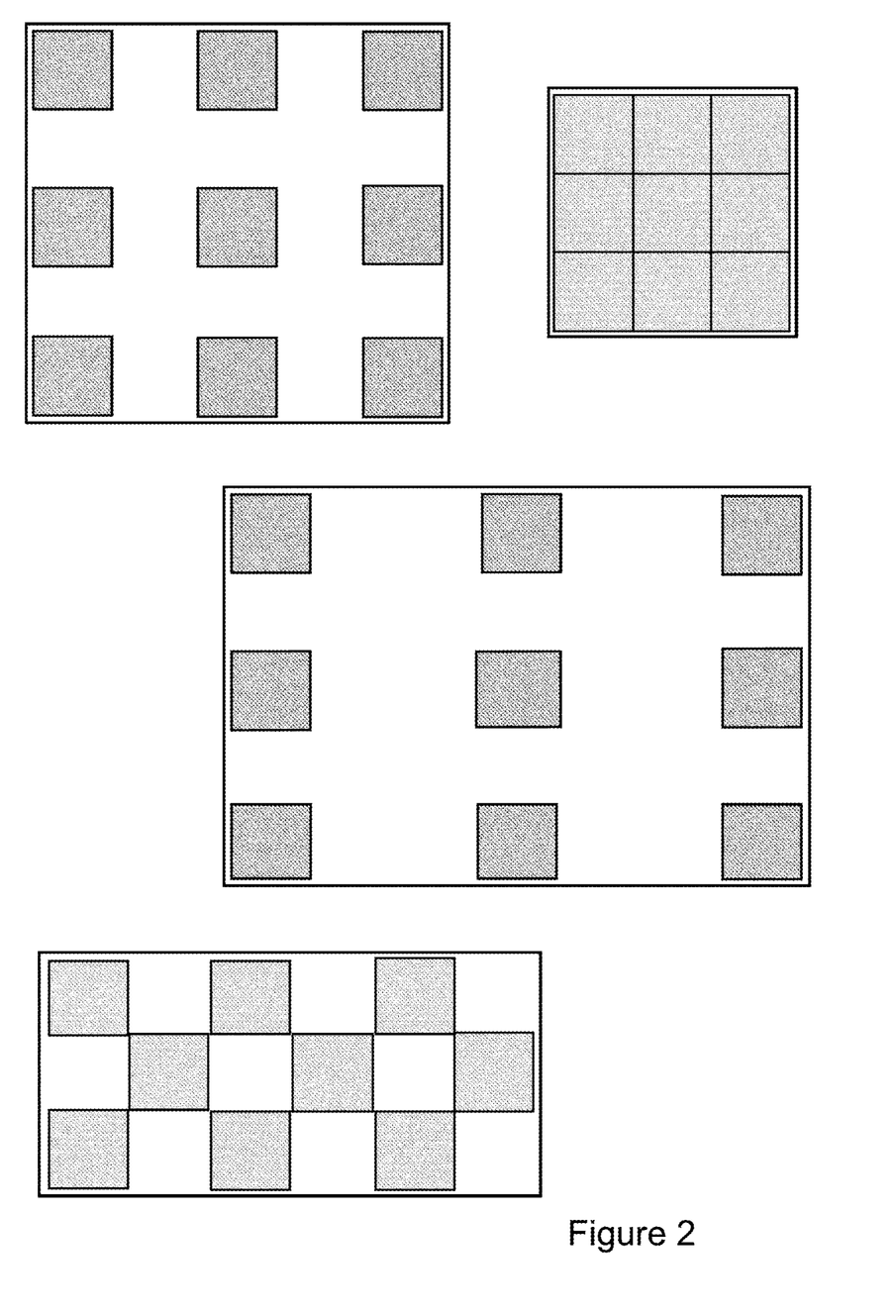
FIG. 2 depicts a selection of patterns that are composed of 9 square individual spots.

In this regard, FIG. 2 shows a selection of patterns composed of 9 square individual spots, wherein the square individual spots feature an edge length of 50 µm. While a shading was omitted in the full-surface pattern in FIG. 1, the individual spots in FIG. 2 are shaded so that the patterns can be recognized more clearly.

While the upper right-hand illustration of FIG. 2 depicts a full-surface pattern, a pattern is shown at the top left, whose individual spots feature a respective distance of one spot size.

For the pattern shown in the center, the distance of the individual spots in vertical direction is one spot size but in horizontal direction it is the double spot size.

The lower illustration also depicts a pattern composed of 9 square individual spots, in which the individual spots are assembled into a "checkerboard pattern" and in which the individual spots touch each other at their corners.

By application of a minimum spot dimension of 50 µm, a treatment for the regeneration of retinal tissue is possible because the migration paths of the RPE cells from the untreated tissue can be kept to a minimum.

In contrast to solutions of the known prior art, in which treatment spots are set with a maximum diameter of 400 µm, the treatment areas can be increased with the method according to the invention to a diameter of approx. 1 mm or also to several mm, since untreated tissue bridges are available for the regeneration.

Figure 3:
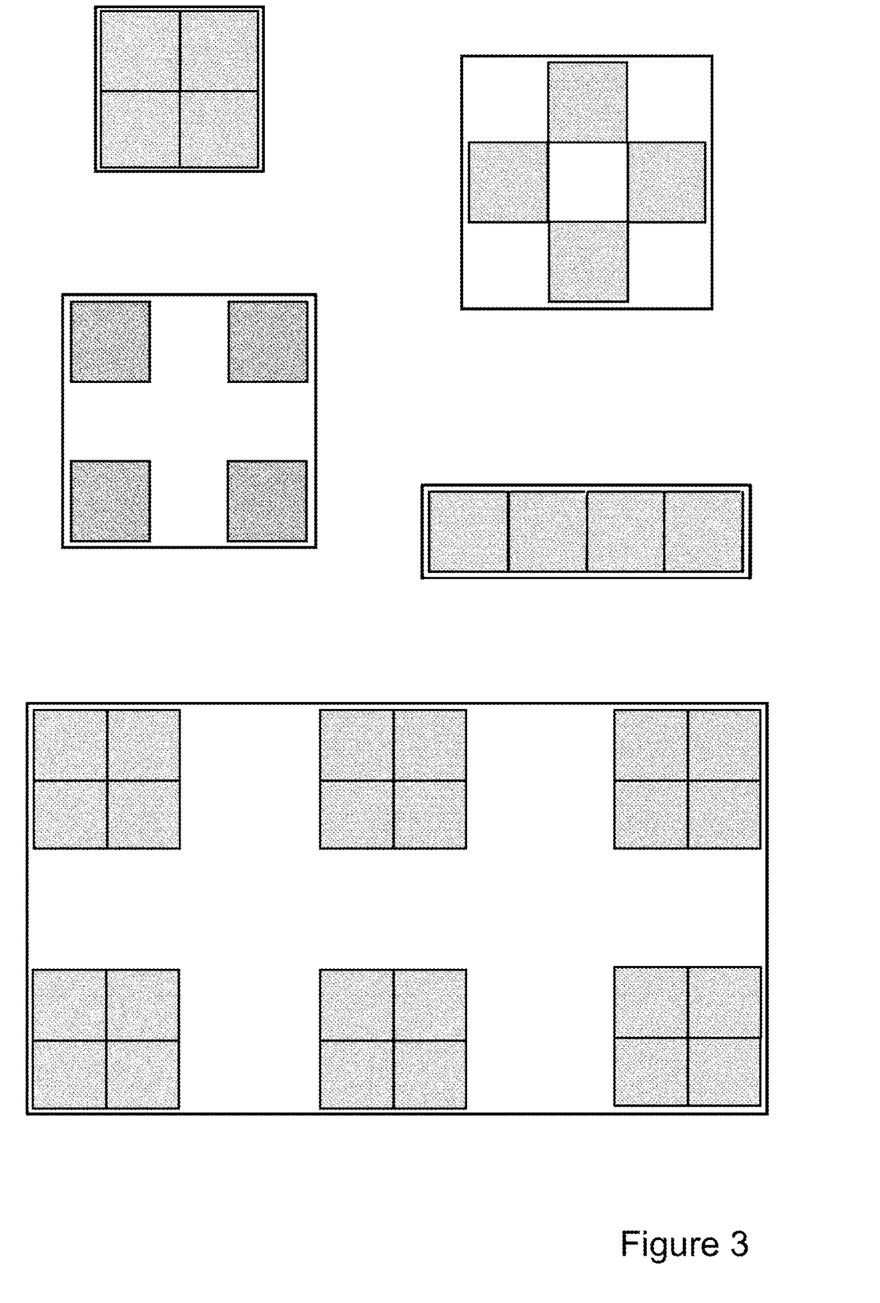
FIG. 3 depicts a selection of patterns that are made up of 4 square individual spots.

In analogy to FIG. 2, FIG. 3 depicts a selection of patterns, which are composed of 4 square individual spots. The individual spots in the patterns are also shaded in this case.

The illustration on the bottom of FIG. 3 depicts a pattern that is based on multi-spots, which are composed of 4 square individual spots with an edge length of 50 µm. The distance between the 6 multi spots amounts to 100 µm. Optionally, the amount of the applied multi spots can vary. Correspondingly, a pattern can also be composed of 4 square individual spots with an edge length of 100 µm. The distance between the 6 multi spots amounts to 200 µm.

As already described, it is also possible to use patterns in the treatment of the retina whose square spots do not feature any distance from each other and thus touch each other. Thus, octagonal patterns in accordance with FIG. 1 are also possible in this case, which are composed e.g. of 52 square laser spots.

Both, the patterns with a distance between the individual spots as well as the full-surface multi spot patterns can be selectively positioned by the physician at the fundus of the eye for the treatment.

Figure 4:
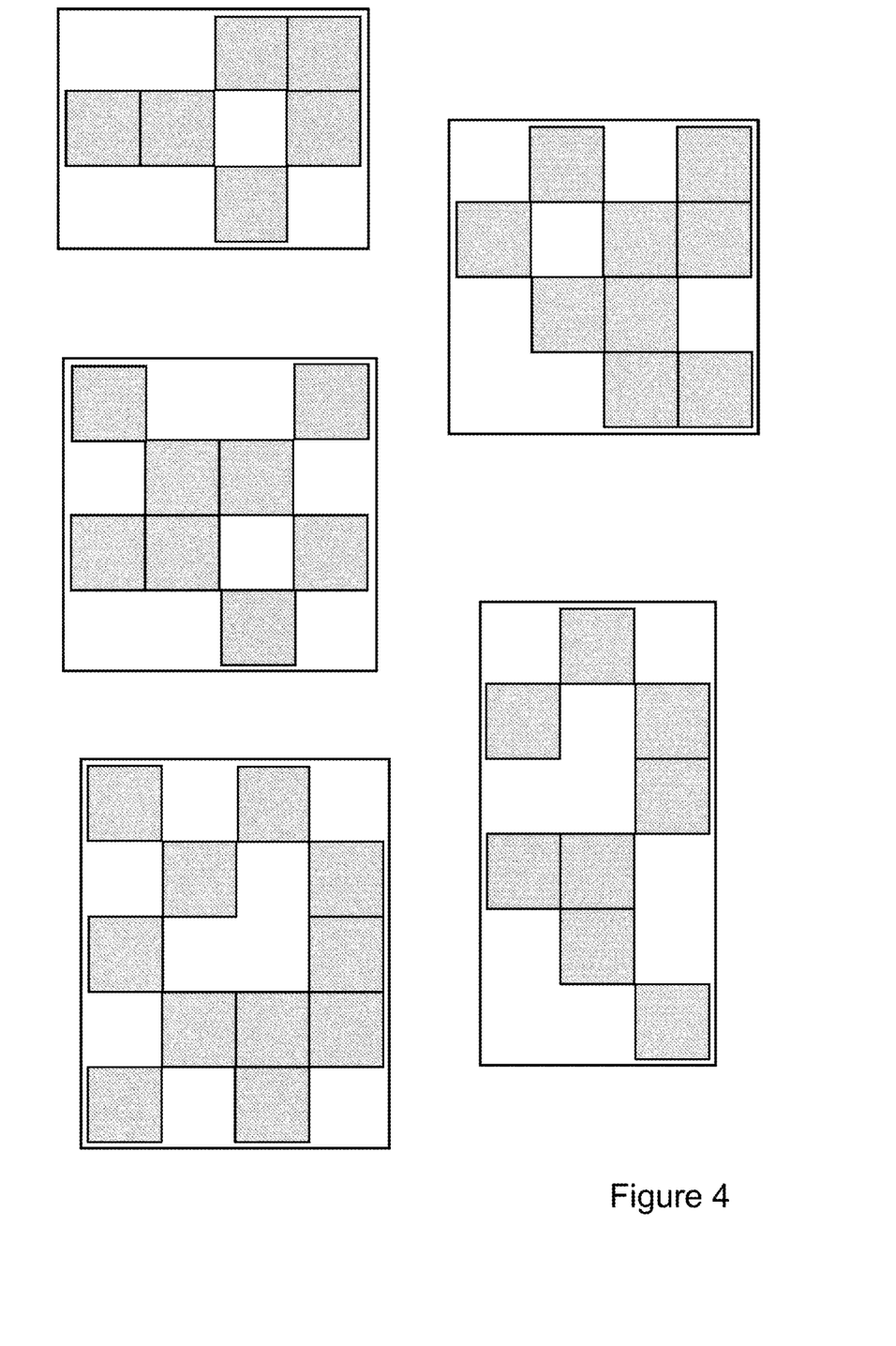
FIG. 4 depicts a selection of individually designed, non-symmetrical patterns.

While a selection of possible symmetrical patterns are depicted in the FIGS. 2 to 3, FIG. 4 shows a selection of individually designed, asymmetrical patterns. It is pointed out that the herein described patterns merely represent a selection. In principle, the patterns can be adapted to any shape of the areas that is to be treated.

According to a further example embodiment, the proposed method is suitable for the thermal millisecond laser coagulation, wherein the solid-state laser emits individual pulses with pulse lengths in the ms-range.

The control unit of the solid-state laser herein determines the size of the center of the damage zone with a lateral and axial expansion from the size of the optical spot at the treatment location, the pulse length, the energy density, wherein the magnification of a contact glass that was used is taken into account. The control unit selects parameter sets for the solid-state laser from the ascertained size of the center of the damaged area.

The thermal size of the center of the damage zone can hereby be preselected for the application and the control unit selects suitable parameter combinations for the solid-state laser from a database.

For the laser coagulation of the retina at pulse lengths in the ms-range, a distinction is made between irreversible damage and reversible damage in the thermal damage zone.

According to example embodiments of the invention, the control unit determines in particular the size of an irreversibly damage center in order to then select the spot distance of the individual pulses in such a way that no overlapping of irreversible damages occurs and that it is optionally possible to regulate additional distances between the irreversibly damage center sizes.

So far, the spot distances within a pattern are pre-programmed. However, with regard to the thermal effect, in particular the size of the irreversible damage is clinically interesting.

Thus, in line with example embodiments of the invention, the size of an irreversibly damaged center is determined in order to select the spot distance in such a way that an overlapping of irreversible damaged center zones is prevented. Optionally, additional distances can be set between the irreversibly damaged centers.

According to a last advantageous example embodiment, the temperature profile can be measured by means of an opto-acoustic detection and can be used as a therapy criterion.

All of the individual spot or multi-spot patterns shown above can be processed according to example embodiments of the invention by application of individual pulses or, in particular also by application of a plurality of laser pulses. A laser pulse repetition of e.g. 30 pulses without interruption can be carried out with a repetition frequency of 100 Hz, 1 kHz or 5 kHz.

The processing can hereby be carried out in such a way that one individual spot of the pattern is completely processed first by application of a pulse sequence, or that the pulse sequence processes the individual spots of the pattern sequentially per respective pulse, wherein multiple pulse repetitions are required.

In the application of pulse sequences, a dosimetry is optionally provided, which reduces the maximum number of pulses, for example, 30 pulses to e.g. 20 pulses due to a threshold signal, such as the formation of a blister or a qualitative alteration in the optical reflection or backscattering of light, if the desired treatment threshold happens before that.

As it was mentioned before, the laser effects are not visible to the attending physician during the therapy and can only be recognized by application of e.g. a subsequent fluorescence angiography on the irradiated areas.

In order to make at least the treatment zones visible to the attending physician and to mark these for further tracking, it is intended in a further embodiment to place visible therapeutic laser lesions on the edge of the retinal area that is to be treated.

In a specific embodiment, individual spots with a pulse length of approximately 1.7 µs at a square spot size of 100 µs are used for the proposed CSLT-method.

Figure 5:
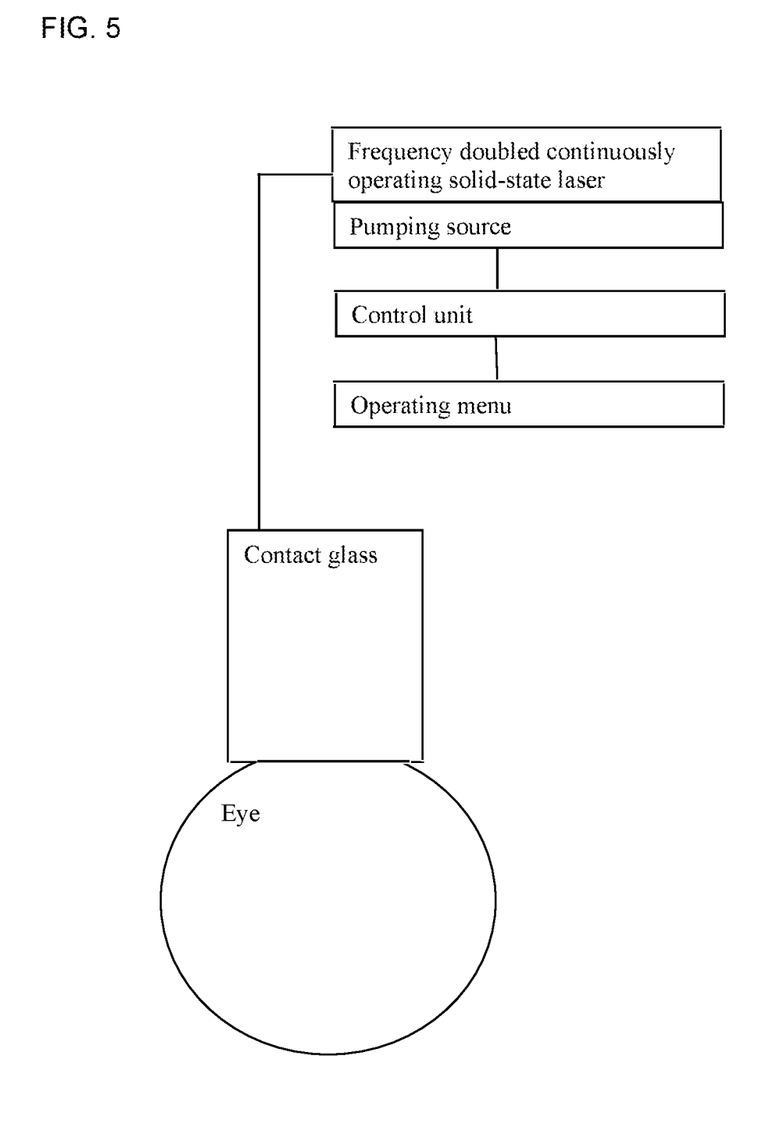
FIG. 5 is a block diagram of a portion of an example embodiment of the invention.

FIG. 5 is a block diagram of a portion of an example embodiment of the invention.

In accordance with a last example embodiment of the method according to the invention, all the patterns mentioned for the SRT therapy can also be used for the 2RT therapy with appropriate adaptation of the pulse energies and/or pulse lengths.

The solution in line with the invention provides a method for a minimally invasive, cell-selective laser therapy on the eye, which is based on a short-pulse laser system and which permits various selective therapy forms in the eye.

The proposed example method for a minimally invasive, cell-selective laser therapy on the eye enables a selective treatment of melanin-containing cells in the different areas of the eye via the targeted control of the pump source. Hereby, an intracellular or cellular therapy can be selected by application of a choice of the pulse length that is flexible from pulse to pulse.

Various embodiments of systems, devices, and methods have been described herein. These embodiments are given only by way of example and are not intended to limit the scope of the claimed inventions. It should be appreciated, moreover, that the various features of the embodiments that have been described may be combined in various ways to produce numerous additional embodiments. Moreover, while various materials, dimensions, shapes, configurations and locations, etc. have been described for use with disclosed embodiments, others besides those disclosed may be utilized without exceeding the scope of the claimed inventions.

Persons of ordinary skill in the relevant arts will recognize that the subject matter hereof may comprise fewer features than illustrated in any individual embodiment described above. The embodiments described herein are not meant to be an exhaustive presentation of the ways in which the various features of the subject matter hereof may be combined. Accordingly, the embodiments are not mutually exclusive combinations of features; rather, the various embodiments can comprise a combination of different individual features selected from different individual embodiments, as understood by persons of ordinary skill in the art. Moreover, elements described with respect to one embodiment can be implemented in other embodiments even when not described in such embodiments unless otherwise noted.

Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims, it is expressly intended that the provisions of 35 U.S.C. § 112(f) are not to be invoked unless the specific terms "means for" or "step for" are recited in a claim.

The invention claimed is:

1. A laser system for a minimally invasive, cell-selective laser therapy at an eye, comprising:
a frequency-doubled, continuously operating solid-state laser with a pumping source and a control unit;
wherein the control unit is configured to regulate the pump source such that the solid-state laser selectively emits individual pulses with pulse lengths between 50 ns and continuous,
wherein the control unit is further configured to allow a user to select the pulse lengths in a first range from 50 ns to 50 µs for selective therapies and in a second range from 50 s to continuously for coagulative or stimulating therapies, and wherein an energy density of the pulses emitted by the laser varies in dependence of the pulse length; and
the laser system further comprising a square optical fiber.

2. The laser system according to claim 1, wherein the solid-state laser emits individual pulses with pulse length in the first range of 50 ns-500 ns, and in the second range of 1 µs-50 µs, wherein the control unit is further configured to allow the user to select application of a single pulse or up to 30 pulses with a pulse repetition rate of 1 Hz up to 10 kHz to be applied per spot on a retina, with spot sizes ranging between 50 µm and 100 µm, wherein single spots are applied or wherein multiple spots are applied which are bundled in the form of pattern whose shape and spot distance are adjustable.

3. The laser system according to claim 2, wherein the solid-state laser emits individual pulses within the first range with a first pulse length of 200 ns and within the second range with a second pulse length of 5 µs.

4. The laser system according to claim 2, wherein the control unit is further configured to allow the user to select the pulse lengths in a range ranging from 50 ns to 500 ns at >50 mJ/cm$^2$ and in a range ranging from of 1 µs-50 µs, with an energy density of an individual pulse of >500 mJ/cm$^2$, for selective laser trabeculoplasty, for selective retina therapy and for retina regeneration therapy.

5. The laser system according to claim 4, wherein the control unit is further configured to allow the user to select the pulse lengths of 5 µs, with an energy density of an individual pulse of >500 mJ/cm$^2$.

6. The laser system according to claim 1, wherein the solid-state laser emits individual pulses with pulse length in the first range of 50 ns-500 ns, with comprising further parameters as follows:
each spot being a square spot having an edge length of 50 µm, and the square spots being arranged in spot patterns with the square spots being directly set adjacent to each other and with the spot pattern having an outer, approximately octagonal shape with a pattern dimension of 400 µm.

7. The laser system according to claim 6, wherein the solid-state laser emits individual pulses with pulse length of 200 ns.

8. The laser system according to claim 6, wherein the solid-state laser emits individual pulses with Pulse energies of 2-50 µJ.

9. The laser system according to claim 8, wherein the solid-state laser emits individual pulses with pulse energies of 25 µJ.

10. The laser system according to claim 1, wherein the control unit is designed to vary the pumping current of the pump source in such a way that the pulse lengths and thus the energy density of the individual pulses of an entire pattern or also of the individual pulses within a pattern are adjustable.

11. The laser system according to the claim 1, wherein the control unit controls the pulse lengths and thus the energy density of the individual pulses of an entire pattern or also of the individual pulses within a pattern are alternating.

12. The laser system according to claim 1, wherein the control unit comprises an operating menu with one or more predetermined parameter sets for different selective therapy forms in the eye.

13. The laser system according to claim 1, wherein the following parameters are taken into account in parameter sets of an operating menu of the control unit: spot size, spot distance, shape of the pattern, pulse length, energy density and number of pulses as well as repetition rate.

14. The laser system according to claim 1, wherein the control unit controls spot sizes for an individual pulse in a range of 50 µm to 100 µm for selective laser trabeculoplasty, laser spots being placed next to each other in a dense packing.

15. The laser system according to claim 14, wherein the control unit controls the laser spots being placed next to each other in the dense packing as a square spot.

16. The laser system according to claim 14, wherein the control unit controls the laser to apply a pattern of square laser spots.

17. The laser system according to claim 14, wherein the control unit controls the laser to apply an octagonal pattern made of 52 square laser spots.

18. The laser system according to claim 1, wherein the control unit controls the laser to apply maximum patterns of 400×400 µm² generated in a trabecular meshwork.

19. The laser system according to claim 1, wherein the solid-state laser is configured to emit a laser wavelength in the green or yellow spectral range that selectively destroys lipofuscin at a retina.

20. The laser system according to claim 1, wherein the solid-state laser is configured to emit a laser wavelength of 532 nm, 561 nm, 577 nm or 586 nm, that selectively destroys lipofuscin at the retina.

21. The laser system according to claim 1, wherein the solid-state laser is configured to emit individual pulses with pulse lengths in the ms-range for thermal millisecond laser coagulation.

22. The laser system according to claim 1, wherein the control unit is configured to calculate a center size of a damage zone with a lateral and axial expansion from a size of an optical spot at a treatment location, a pulse length, an energy density and to thereby take into account a magnification of a contact glass that was used.

23. The laser system according to claim 1, wherein the control unit is configured to select parameter sets for the solid-state laser from an ascertained center size of a damage area.

24. The laser system according to claim 1, wherein the control unit is configured to determine the size of an irreversibly damaged center to then select a spot distance of the individual pulses in such a way that no overlapping of irreversible damage occurs.

25. The laser system according to claim 1, wherein the control unit is configured to regulate additional distances between the irreversibly damaged center sizes.

26. The laser system according to claim 1, wherein the control unit is configured to measure a course of a temperature by opto-acoustic detection and to use the temperature as a therapy criterion.

27. The laser system according to claim 1, wherein the control unit is coupled to a sensor configured to detect an emergence of a blister or a qualitative alteration in an optical reflection or backscattering of light, to reduce a maximum number of pulses if a treatment threshold is reached.

28. A laser system for selective laser trabeculoplasty, wherein a solid-state laser emits individual pulses with pulse length in a range of 50 ns-500 ns, with spot sizes of 50 µm to 100 µm for an individual pulse, wherein square laser spots are applied to a tissue area in close contact adjacent one another within a pattern and are densely packed and the pattern completely covers a surface of the tissue area, with a maximum pattern dimension of 400×400 µm².

29. The laser system for selective laser trabeculoplasty, according to claim 28, wherein the solid-state laser emits individual pulses with the pulse length of 200 ns.

30. The laser system for selective laser trabeculoplasty, according to claim 28, wherein the individual pulse are set for dense packing as square spots adjacent to each other.

31. The laser system according to claim 28, wherein the solid-state laser emits individual pulses in a form of the square spots with an edge length of 50 µm and spot patterns with the square spots that are directly set adjacent to each other with an outer, approximately octagonal shape with a pattern dimension of 400 µm.

32. The laser system according to claim 29, wherein the solid-state laser emits individual pulses with pulse energies of 2-50 µJ.

33. The laser system according to claim 29, wherein the solid-state laser emits individual pulses with pulse energies of 25 µJ.

* * * * *

UNITED STATES PATENT AND TRADEMARK OFFICE
CERTIFICATE OF CORRECTION

PATENT NO. : 11,660,231 B2
APPLICATION NO. : 17/202530
DATED : May 30, 2023
INVENTOR(S) : Dick et al.

It is certified that error appears in the above-identified patent and that said Letters Patent is hereby corrected as shown below:

In the Specification

Column 1, Line 9, delete "2018" and insert --2018, now Pat. No. 10,973,687,--

Column 2, Line 10, delete "1800" and insert --180°--

Column 4, Line 15, delete "rage" and insert --range--

Column 5, Line 57, delete "3600 and insert --360°--

In the Claims

Column 9, Line 60, delete "50 s" and insert --50 µs--

Column 10, Line 16, delete "from of" and insert --from--

Column 10, Line 39, delete "Pulse" and insert --pulse--

Column 12, Line 20, delete "µm2." and insert --µm$^2$.--

Signed and Sealed this
Third Day of September, 2024

Katherine Kelly Vidal
*Director of the United States Patent and Trademark Office*